(12) United States Patent
Aquino Maier et al.

(10) Patent No.: US 10,502,680 B2
(45) Date of Patent: Dec. 10, 2019

(54) LIGHT GUIDE DEVICE, MEASUREMENT SYSTEM, AND METHOD FOR PRODUCING A LIGHT GUIDE DEVICE

(71) Applicant: Robert Bosch GmbH, Stuttgart (DE)

(72) Inventors: Daniel Aquino Maier, Stuttgart (DE); Martin Schreivogel, Stuttgart (DE); Philipp Elmlinger, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 15/758,057

(22) PCT Filed: Aug. 17, 2016

(86) PCT No.: PCT/EP2016/069511
§ 371 (c)(1),
(2) Date: Mar. 7, 2018

(87) PCT Pub. No.: WO2017/042008
PCT Pub. Date: Mar. 16, 2017

(65) Prior Publication Data
US 2018/0252635 A1    Sep. 6, 2018

(30) Foreign Application Priority Data

Sep. 11, 2015    (DE) ........................ 10 2015 217 425

(51) Int. Cl.
*G01N 21/25*    (2006.01)
*G01N 21/3504*    (2014.01)
(Continued)

(52) U.S. Cl.
CPC .......... *G01N 21/255* (2013.01); *G01N 21/33* (2013.01); *G01N 21/3504* (2013.01); *G02B 6/00* (2013.01);
(Continued)

(58) Field of Classification Search
CPC ........... G01N 21/431; G01N 2021/433; G01N 21/522; G01N 21/553; G01N 21/554
See application file for complete search history.

(56) References Cited

U.S. PATENT DOCUMENTS 4,872,759 A    10/1989    Stich-Baumeister et al.
5,359,681 A *  10/1994    Jorgenson ............ G01N 21/553
                                                   250/227.11
(Continued)

FOREIGN PATENT DOCUMENTS

DE    35 86 622 T2    1/1993
DE    102 04 531 A1    8/2003
(Continued)

OTHER PUBLICATIONS

International Search Report corresponding to PCT Application No. PCT/EP2016/069511, dated Nov. 14, 2016 (German and English language document) (9 pages).
(Continued)

*Primary Examiner* — Shawn Decenzo
(74) *Attorney, Agent, or Firm* — Maginot, Moore & Beck LLP

(57) ABSTRACT

A light guide device for conducting a light beam between a light source and a measuring unit for measuring a gas or substance concentration includes a light conductor and a holding apparatus. The conductor includes at least one coupling section, which faces, or can be arranged to be turned toward, the light source, for coupling the light beam, and a decoupling section, which faces, or can be arranged to be turned toward, the measuring unit, for decoupling the light beam. The conductor is configured to conduct the light beam between the coupling section and the decoupling section via total reflection on a boundary surface to a fluid or material that surrounds the conductor and has a smaller refractive index than the conductor. The holding apparatus is
(Continued)

configured to hold the conductor in the fluid such that at least one primary portion of a surface of the conductor contacts the fluid.

14 Claims, 6 Drawing Sheets

(51) Int. Cl.
*G01N 21/33* (2006.01)
*G02B 6/00* (2006.01)
*G02B 6/42* (2006.01)

(52) U.S. Cl.
CPC ......... *G02B 6/4206* (2013.01); *G02B 6/4219* (2013.01); *G02B 6/4266* (2013.01); *G01N 2201/0806* (2013.01); *G01N 2201/0873* (2013.01)

(56) References Cited

U.S. PATENT DOCUMENTS

| | | | | |
|---|---|---|---|---|
| 5,439,647 | A * | 8/1995 | Saini | G01N 21/431 250/227.14 |
| 2003/0235369 | A1 | 12/2003 | Grosjean et al. | |
| 2004/0081384 | A1 * | 4/2004 | Datesman | G01N 21/431 385/12 |
| 2008/0013877 | A1 * | 1/2008 | Schmidt | G01N 21/0303 385/12 |
| 2009/0279074 | A1 * | 11/2009 | Seaver | G01N 21/4133 356/73 |
| 2010/0177310 | A1 * | 7/2010 | Difoggio | E21B 47/00 356/326 |
| 2010/0296080 | A1 * | 11/2010 | Nishikawa | G01D 5/35383 356/128 |
| 2011/0168876 | A1 * | 7/2011 | Hsiao | G01N 21/4133 250/215 |
| 2011/0267603 | A1 * | 11/2011 | Shaw | G01N 21/431 356/128 |
| 2012/0069328 | A1 * | 3/2012 | Wootten | G01N 21/431 356/133 |
| 2013/0045541 | A1 | 2/2013 | Fix et al. | |
| 2014/0264030 | A1 * | 9/2014 | Lin | G02B 6/136 250/338.4 |
| 2014/0354979 | A1 * | 12/2014 | Li | G01N 21/41 356/128 |
| 2014/0373606 | A1 * | 12/2014 | Kraiczek | G01N 33/54373 73/61.55 |
| 2016/0231233 | A1 * | 8/2016 | Wang | G01N 21/3504 |
| 2016/0266110 | A1 * | 9/2016 | Ozdemir | G01N 15/1434 |
| 2017/0182978 | A1 * | 6/2017 | Backes | G02B 3/005 |
| 2017/0292374 | A1 * | 10/2017 | Tackmann | G01N 21/552 |
| 2018/0011010 | A1 * | 1/2018 | Chang | B01J 20/06 |
| 2019/0033205 | A1 * | 1/2019 | Egalon | G01N 21/17 |

FOREIGN PATENT DOCUMENTS

| | | |
|---|---|---|
| DE | 10 2012 103 628 A1 | 10/2013 |
| EP | 0 171 615 A2 | 2/1986 |
| EP | 1 846 923 B1 | 4/2009 |

OTHER PUBLICATIONS

Yang et al.; Design of suspended SU-8 optical waveguides for ultrasmall bending; Asia Communications and Photonics Conference and Exhibition; Nov. 2, 2009; pp. 1-7; vol. 7630; IEEE.

Tong et al; Subwavelength-diameter silica wires for microscale optical components; The International Society for Optical Engineering; Apr. 2005; pp. 105-112; vol. 5723; SPIE, Bellingham, WA, USA.

Yang et al; Freestanding waveguides in silicon; Applied Physics Letters; Jun. 13, 2007; pp. 1-3; vol. 90, Issue No. 24; American Institute of Physics Publishing LLC, USA.

Siebert, Ralph et al., Infared integrated optical evanescent field sensor for gas analysis Part II. Fabrication, Sensors and Actuators A: Physical, Bd. 119, Nr. 2 pp. 584-592 (Apr. 13, 2005), XP027806965.

Sekiya T. et al., "Design, fabrication, and optical characteristics of freestanding GaN waveguides on silicon substrate", Journal of Vacuum Science & Technology B: Microelectronics and Nanometer Structures, Bd. 33, Nr. 3 (May 1, 2015), XP055547480

* cited by examiner

LIGHT GUIDE DEVICE, MEASUREMENT SYSTEM, AND METHOD FOR PRODUCING A LIGHT GUIDE DEVICE

This application is a 35 U.S.C. § 371 National Stage Application of PCT/EP2016/069511, filed on Aug. 17, 2016, which claims the benefit of priority to Serial No. DE 10 2015 217 425.5, filed on Sept. 11, 2015 in Germany, the disclosures of which are incorporated herein by reference in their entirety.

BACKGROUND

The disclosure proceeds from a generic apparatus or method according to the independent claims. The subject matter of the present disclosure also relates to a computer program.

As a rule, light guides such as optical fibers or optical waveguides, for example, consist of a core and a cladding, with the light-guiding effect based on total-internal reflection arising on account of the core having a higher refractive index in comparison with the cladding.

Particularly in the field of telecommunications, the differences between the refractive indices may be very small, for instance less than 0.05.

Light guides for sensor applications, such as, for instance, in the field of absorption spectroscopy, may be embodied, for example, to split, for reference measurements, a light beam emanating from a light source and, in the process, guide as much light as possible to a sensitive unit. The light beam can be split with the aid of, for instance, plane light guide structures such as Y-couplers.

SUMMARY

Against this background, the approach here is used to present a light guide apparatus for guiding a light beam between a light source and a measuring unit for measuring a gas concentration, a measurement system, a method for producing a light guide apparatus, furthermore an apparatus using said method, and, finally, a corresponding computer program according to the main claims. By way of the measures listed in the dependent claims, advantageous developments and improvements of the apparatus specified in the independent claim are possible.

A light guide apparatus for guiding a light beam between a light source and a measuring unit for measuring a substance concentration is presented, wherein the light guide apparatus has the following features:

a light guide having, for the purposes of coupling in the light beam, at least one input coupling portion that faces or is able to face the light source and, for the purposes of decoupling the light beam, an output coupling portion that faces or is able to face the measuring unit, wherein the light guide is embodied to guide the light beam between the input coupling portion and the output coupling portion by virtue of total-internal reflection at an interface to a fluid or material that surrounds the light guide and that has a lower refractive index than the light guide; and a holding device embodied to hold the light guide in the fluid in such a way that at least a main proportion of a surface of the light guide has contact with the fluid.

A light guide can be understood to mean a transparent component, for instance in the form of a straight, curved or branched rod or beam. In particular, the light guide may be suitable for use in miniaturized systems. Here, the light guidance is achieved by reflection at an interface of the light guide, either as a result of total-internal reflection on account of a lower refractive index of the fluid surrounding the light guide or else as a result of mirroring at the interface. By way of example, the light source can be one or more light-emitting diode(s) or one or more laser diode(s). By way of example, the light source can also have one or more reflection elements, such as mirrors, to guide light emitted by a light-emission unit of the light source into a desired light output direction of the light source. A section of a surface of the light guide, in particular e.g. a cross-sectional area, can be understood to be an input or output coupling portion. The cross-sectional area may be, for instance, rectangular, round or hexagonal. By way of example, a measuring unit can be understood to mean a measurement cell, a measurement detector or a reference detector. The fluid can be a gas or a gas mixture such as air, for instance, or else a liquid such as oil, for instance. The material can be a transparent material such as a silicone material, for example. In order to avoid contamination and measurement errors resulting therefrom, the light guide can be arranged or arrangeable in a housing that is filled or able to be filled with the fluid or material and that is able to be sealed in a fluid-tight manner, for example. A holding device can be understood to mean a holder for fastening or placing the light guide. By way of example, the holding device can be connected to the light guide by force fit, in an interlocking manner or in an integrally bonded manner. However, an integral embodiment of the light guide and the holding device is also conceivable, with it being possible for the light guide and the holding device to be manufactured from the same material.

The approach described here is based on the discovery that it is possible to realize a compact and robust light guide system using a cladding-free light guide and a corresponding holder for positioning or anchoring the light guide in a medium forming an interface with the light guide, said light guide system facilitating a comparatively simple integration of optical components such as curves, mode mixers, splitters and Y-couplers, for example, depending on the embodiment. As a result of a correspondingly thick core layer of the light guide, it is possible to ensure high input coupling, particularly in conjunction with so-called butt coupling, for instance, but also when coupling-in collimated light. Moreover, this renders it possible to obtain a high refractive index difference in relation to the light guide and the medium surrounding the latter, as a result of which there is, in turn, a large acceptance angle for efficient input coupling of light.

Advantageously, such a light guide apparatus may have a high transmission for light beams in the UV range from 200 to 400 nm and it may, moreover, be solarization-resistant. Consequently, the light guide apparatus is well-suited for applications in absorption spectroscopy, in particular in UV absorption spectroscopy for the optical detection of (exhaust) gases such as, for instance, nitrogen oxides (NO, $NO_2$) and sulfur oxides ($SO_2$), and ammonia ($NH_3$) or ozone ($O_3$).

By way of example, the light guide apparatus can be realized in the form of a free-standing glass core light guide with air-vacuum cladding. The advantage of such a light-guiding system consists of as much light as possible being able to be coupled-in and guided with, at the same time, elements such as couplers being made possible. Furthermore, it is advantageous that the light guide apparatus makes do without lens elements and it is miniaturizable. As a result of this, it is possible, firstly, to reduce the production costs; secondly, this allows the production to be simplified and the robustness to be increased. By way of example, external optical elements such as mirrors or lens elements may be dispensed with in the case of a miniaturized and hence correspondingly compact light guide apparatus, as a result of which the adjustment outlay and hence the production costs can be significantly reduced. It is also possible to dispense with some of the elements specified here, with optical elements, which may also be integrated in a light source, possibly being required for input/output coupling of light into the measurement cell.

According to an embodiment, the light guide apparatus may have a base element for receiving the holding device. In particular, the base element can be manufactured from silicon or a silicon-containing material. By way of example, the base element may be formed with a corresponding cut-out or recess in order to facilitate contact between the light guide and the fluid that is as extensive as possible. The base element allows the holding device to be supported in a stable manner.

It is also advantageous if the light guide and the holding device have an integral embodiment. Alternatively, or additionally, the light guide and the holding device may be embodied from the same material. This embodiment facilitates an embodiment of the light guide apparatus that is as stable as possible while having comparatively low production costs.

Further, it is advantageous if the input coupling portion is formed by a cross-sectional area of a first end of the light guide and the output coupling portion is formed by a cross-sectional area of a second end of the light guide. By way of example, the light guide can be manufactured as a bar having a rectangular or hexagonal cross section and corresponding cross-sectional areas as input and output coupling portion. The light guide can be produced very easily by this embodiment, too.

According to a further embodiment, the light guide and, additionally or alternatively, the holding device can be manufactured from glass and/or a polymer. Such materials offer the advantage of low production costs and good transmission properties, particularly in the wavelength range of UV light.

According to a further embodiment, it may be advantageous to provide a temperature regulating unit for active and/or passive cooling and/or heating of the light source and/or of the light guide and/or of the measuring unit. That is to say that, expressed differently, the light source and/or the light guide and/or measuring units connected to the light guide, such as e.g. photodetectors or an absorption measurement cell, are coupled to active and/or passive temperature regulators or cooling elements. By way of example, such a temperature regulator can be realized by a Peltier element. Such an apparatus may be advantageous, particularly in absorption spectroscopy of exhaust gases, in order to ensure the function of temperature-sensitive elements, such as e.g. LEDs or photodetectors, in surroundings with a high heat development or strong temperature variations, such as e.g. in the exhaust branch of combustion engines. Further, it is possible to ensure the same or a constant spectral sensitivity and hence eliminate or reduce the temperature dependence by regulating the temperature of elements such as photodetectors, which, for example, may be attached to different light guide branches and be exposed to different temperatures.

Moreover, the holding device may comprise at least one first holding element and one second holding element. The light guide may be clamped or able to be clamped between the first holding element and the second holding element. In particular, the first holding element or, additionally or alternatively, the second holding element can have a U-shaped or L-shaped configuration. By way of example, the two holding elements can be interconnected to form a frame. The light guide apparatus can have a very compact embodiment as a result of such a holding device.

Here, the first holding element can have a cross section that tapers in the direction of the light guide at at least one contact point at which the first holding element contacts the light guide. Accordingly, alternatively or additionally, the second holding element can also have a cross section that tapers in the direction of the light guide at at least one contact point at which the second holding element contacts the light guide. By way of example, the cross section can taper to a point. As a result, light losses when guiding the light beam through the light guide can be reduced.

Further, at at least one branching point, the light guide can have at least one light guide branch for deflecting and/or splitting a light beam, coupled-in via the input coupling portion or the output coupling portion, into at least two partial beams. By way of example, the light guide branch can be a secondary branch of the light guide that is connected to a main branch that has the input and output coupling portion. Here, depending on the embodiment, the light guide branch can be arranged on the main branch at right angles or with an acute angle, for example. In a manner analogous to the main branch, the light guide branch may also have a corresponding output coupling portion for decoupling one of the two partial beams. As a result of this embodiment, the light beam can be steered simultaneously in different directions. In particular, the light guide can be realized as a Y-shaped coupler, for example. Advantageously, the light guide branch may also act as a holding element for simultaneously holding the light guide.

According to a further embodiment, the light guide can have at least one first light guide branch at at least one first branching point and at least one second light guide branch at at least one second branching point. The first branching point can be embodied to split a light beam, coupled-in via the input coupling portion, into a first partial beam and a second partial beam in such a way that the first partial beam is steered to the output coupling portion and the second partial beam is steered into the first light guide branch. Additionally, or alternatively, the second branching point can be embodied to steer a light beam, coupled-in via the output coupling portion, into the second light guide branch and/or split said light beam into a third partial beam and a fourth partial beam in such a way that the third partial beam is steered toward the input coupling portion and the fourth partial beam is steered into the second light guide branch. In particular, the second branching point can be embodied to steer the light beam, coupled-in via the output coupling portion, and/or the fourth partial beam into a direction that deviates from a direction of the light beam that is coupled-in via the input coupling portion or of the first partial beam or of the second partial beam. Depending on the embodiment, the two light guide branches may be arranged on mutually adjacent or opposing sides of the light guide. As a result of this embodiment, too, the light guide apparatus can be realized in a particularly space-saving manner with comparatively few parts.

It is also particularly expedient if the light guide according to a further embodiment is formed to homogenize the light beam. By way of example, the light guide may have a spiral-shaped or wave-shaped structure to this end, at least in portions. As a result of this embodiment, additional optical elements for homogenizing the light beam can be dispensed with.

The approach described here further develops a measurement system having the following features:

a light guide apparatus according to one of the above embodiments;

a light source that is arranged facing the input coupling portion of the light guide; and a measuring unit for measuring a gas concentration or substance concentration, wherein the measuring unit is arranged opposite the output coupling portion of the light guide.

The light source or a light-emitting element need not necessarily be arranged opposite the input coupling portion (in the form of parallel planes). By way of example, it is also possible to use deflection mirrors such that the emitting area and the light guide may be installed horizontally.

Moreover, the approach proposed here develops a method for producing a light guide apparatus according to one of the above embodiments, wherein the method includes the following steps:

forming the light guide by processing a provided substrate made out of a light-guiding material; and arranging the light guide in a provided holding device.

Alternatively, both the light guide and the holding device are formed by processing the substrate within the forming step, for instance within the scope of a suitable cutting or etching method. Here, depending on the embodiment, the light guide is shaped on the holding device and/or the holding device is shaped on the light guide. Here, the arrangement step can be dispensed with.

This method can be implemented, for example, in software or hardware or in a mixed form of software and hardware, for example in a control device.

The approach presented here further develops an apparatus embodied to perform, actuate or implement the steps of a variant of a method presented here in appropriate devices. By way of this embodiment variant of the disclosure in the form of an apparatus, too, the object underlying the disclosure can be solved in a quick and efficient manner.

In the present case, an apparatus can be understood to mean an electrical appliance which processes sensor signals and outputs control and/or data signals independence thereon. The apparatus may have an interface which can be embodied in terms of hardware and/or software. In the case of an embodiment in the form of hardware, the interfaces may be part of a so-called system ASIC, for example, which contains very different functions of the apparatus. However, it is also possible for the interfaces to be dedicated, integrated circuits or to consist at least partly of discrete components. In the case of an embodiment in terms of software, the interfaces may be software modules which are present, for example, on a microcontroller in addition to other software modules.

A computer program product or computer program with program code that may be stored on a machine-readable carrier or storage medium, such as a semiconductor storage device, a hard disk storage device or an optical storage device, and that is used to perform, implement and/or actuate the steps of the method according to one of the embodiments described above is also advantageous, particularly if the program product or program is executed on a computer or an apparatus.

BRIEF DESCRIPTION OF THE DRAWINGS

Exemplary embodiments of the disclosure are illustrated in the drawings and explained in more detail in the following description. In the figures.

DETAILED DESCRIPTION

In the following description of expedient exemplary embodiments of the present disclosure, the same or similar reference signs are used for the elements with a similar effect that are illustrated in the various figures, with a repeated description of these elements being forgone.

Figure 1:
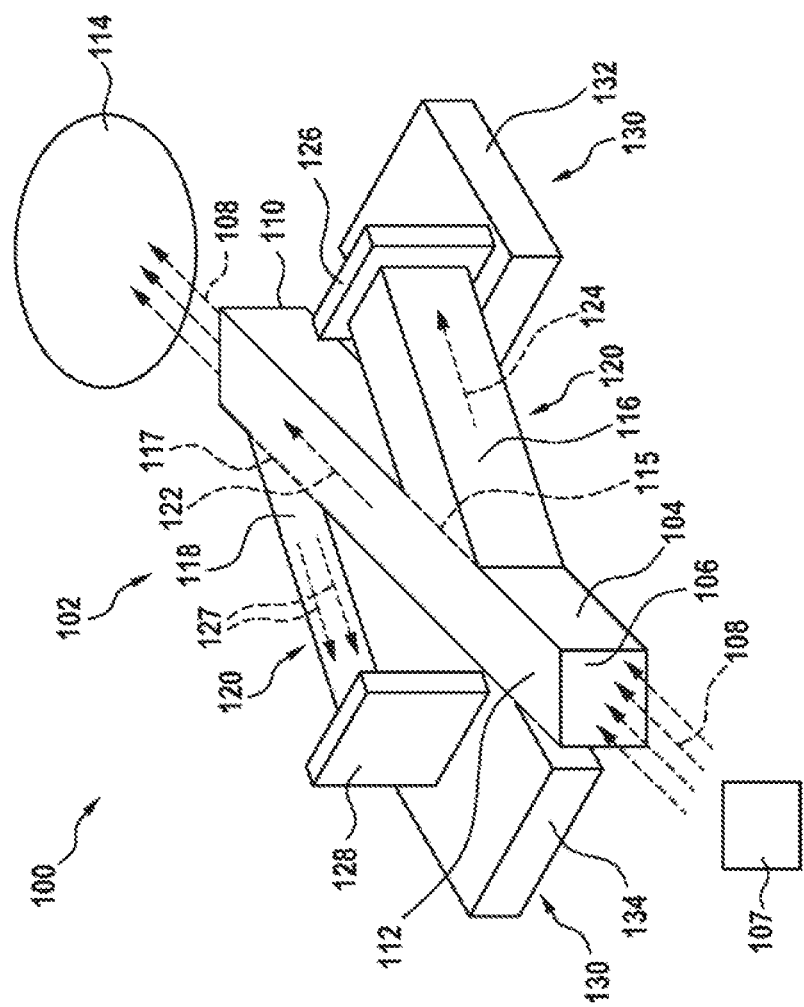
FIG. 1 shows a schematic illustration of a measurement system according to an exemplary embodiment.

FIG. 1 shows a schematic illustration of a measurement system 100 according to an exemplary embodiment. The measurement system 100 comprises a light guide apparatus 102 made of a light guide 104 with an input coupling portion 106 for coupling-in a light beam 108 emitted by a light source 107 that is arranged facing the input coupling portion 106 and with an output coupling portion 110 for decoupling the light beam 108. According to this exemplary embodiment, the light guide 104 is realized with a beam-like main branch 112, with the input coupling portion 106 being formed by a rectangular cross-sectional area of a first end of the main branch 112 and the output coupling portion 110 being formed by a likewise rectangular cross-sectional area of a second end of the main branch 112 lying opposite the first end. Further, it is conceivable that the cross-sectional area of the first and/or second end is formed with a form that differs from that of a rectangle, for example a hexagonal form or any polygonal form. Moreover, such a cross-sectional area need not necessarily be planar. A measurement cell is arranged as a measuring unit 114 in a manner facing, or able to face, the output coupling portion 110, and so the light beam 108 emerging from the output coupling portion 110 is incident on the measuring unit 114.

According to the exemplary embodiment shown in FIG. 1, the light guide apparatus 102 has a first light guide branch 116 at a first branching point 115 and a second light guide branch 118 at a second branching point 117; here, these are arranged on mutually opposite sides of the main branch 112 in an exemplary manner. Firstly, the two light guide branches 116, 118 serve as a holding device 120 for holding the light guide 104 in a fluid with a lower refractive index than a material of the light guide 104. Secondly, the first light guide branch 116 serves to split the light beam 108, coupled-in via the input coupling portion 106, into a first partial beam 122 and a second partial beam 124, with the first partial beam 122 being guided through the main branch 112 to the output coupling portion 110 and the second partial beam 124 being guided through the first light guide branch 116 to a reference detector 126 arranged at one end of the first light guide branch 116.

Like the main branch 112, the two light guide branches 116, 118 are realized as straight beams and are each arranged on the main branch 112 with an acute or obtuse angle in such a way that an end of the first light guide branch 116 points in a direction facing the output coupling portion 110 and an end of the second light guide branch 118 points in a direction facing the input coupling portion 106. Here, the first branching point 115 is arranged adjacent to the input coupling portion 106 and the second branching point 117 is arranged adjacent to the output coupling portion 110. As shown in FIG. 1, the two light guide branches 116, 118 may be aligned substantially parallel to one another.

According to the exemplary embodiment shown in FIG. 1, the second light guide branch 118 serves to steer a light beam 127, reflected from the measuring unit 114 onto the output coupling portion 110, onto a measurement detector 128 placed opposite one end of the second light guide branch 118.

By way of example, the two light guide branches 116, 118 and the main branch 112 are manufactured in one piece from the same material, for instance by way of a suitable cutting or etching method. Depending on the embodiment, the three branches may have an identical cross-sectional area or different cross-sectional areas.

Moreover, the light guide apparatus 102 has an optional base element 130 which, according to the exemplary embodiment shown in FIG. 1, is realized in a two-part form with a first plate 132 and a second plate 134, with the first light guide branch 116 being anchored to the first plate 132 by way of the reference detector 126 attached to the end of the first light guide branch 116 and the second light guide branch 118 being anchored to the second plate 134 by way of the measurement detector 128 attached to the end of the second light guide branch 118. Here, the light guide 104 is arranged freely between the two plates 132, 134 and consequently surrounded by the fluid apart from the connection faces of the two light guide branches 116, 118 at the two branching points 115, 117.

The reference detector 126 and the measurement detector 128 each protrude beyond a respective cross-sectional area of the ends of the two light guide branches 116, 118.

Figure 2:
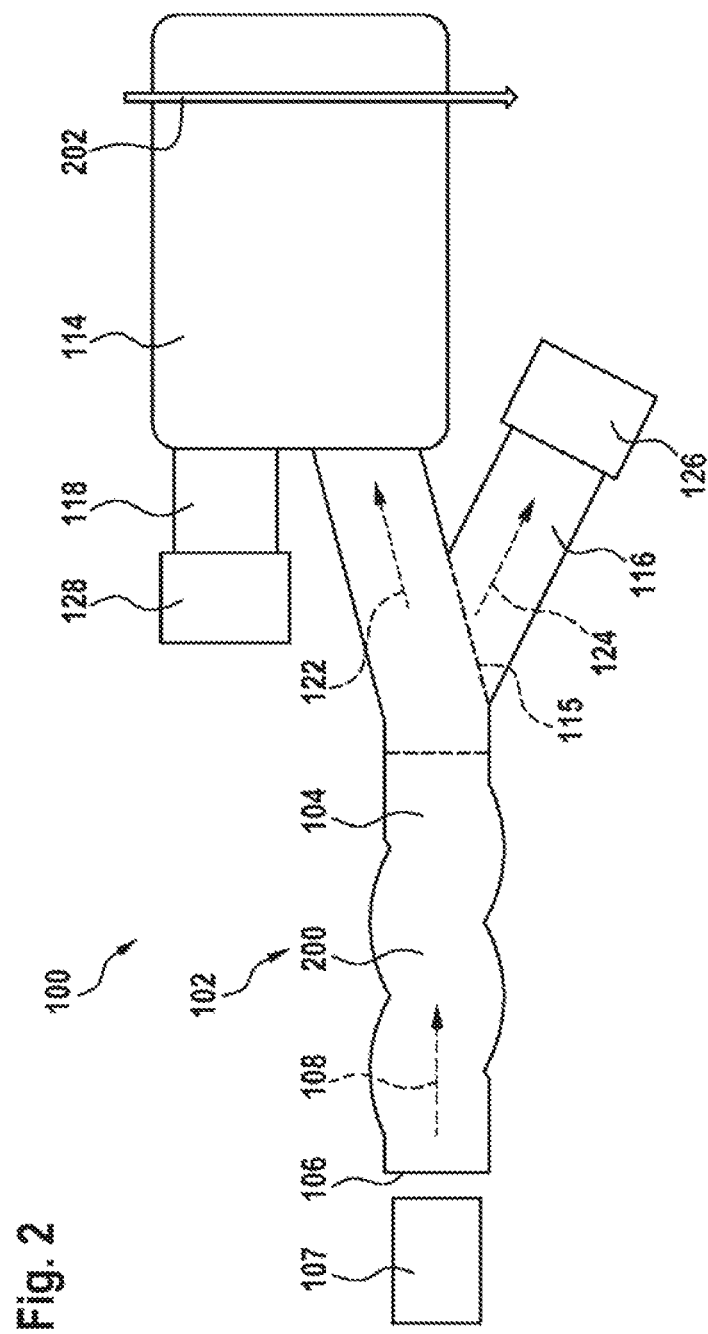
FIG. 2 shows a schematic illustration of a measurement system according to an exemplary embodiment.

FIG. 2 shows a plan view of a schematic illustration of a measurement system 100 according to an exemplary embodiment. In contrast to the measurement system described on the basis of FIG. 1, the main branch 112 of the light guide apparatus 102 according to FIG. 2 is optically coupled to the second light guide branch 118 via the measuring unit 114. Further, between the input coupling portion 106 and the first branching point 115, the light guide branch 104 has an optional homogenization portion 200, acting as a mode mixer, for homogenizing the light beam 108 that has been coupled-in via the input coupling portion 106, said homogenization portion being realized in spiral-shaped fashion in FIG. 2 in an exemplary manner. Here, the first branching point 115 is embodied as a splitter in order to split the light beam 108 into the two partial beams 122, 124.

By way of example, the measuring unit 114 has a mirroring element 202 which is aligned in such a way that the first partial beam 122, which is guided into the measuring unit 114, is reflected forward by the measuring unit 114 in the direction of the second light guide branch 118. In particular, the mirroring element 202 is situated here in a region of the measuring unit 114 that is distant from the light guide 104 such that a path length traveled by the first partial beam 122 in the measuring unit 114 is increased proportionally with a measurement signal. Alternatively, the measuring unit 114 can be realized as a simple irradiation measurement cell or multi-reflection cell. For the purposes of measuring substance concentrations by means of absorption spectroscopy, the medium to be measured can flow through the measurement cell.

Figure 3:
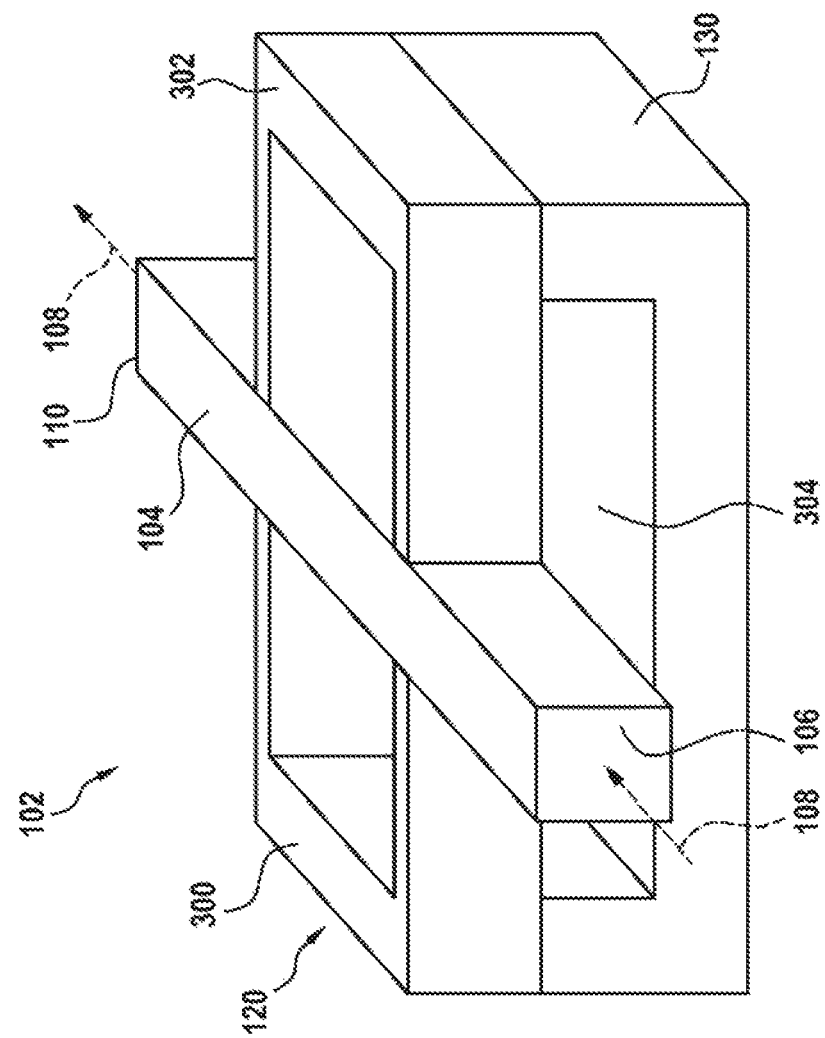
FIG. 3 shows a schematic illustration of a light guide apparatus according to an exemplary embodiment.

FIG. 3 shows a schematic illustration of a light guide apparatus 102 according to an exemplary embodiment. The light guide apparatus 102 is a light guide apparatus that can be used, for example, in a measurement system described above on the basis of FIGS. 1 and 2. According to FIG. 3, the light guide apparatus 102 is realized with a light guide 104 in the form of a straight beam with a rectangular cross-section, which is clamped between two U-shaped holding elements 300, 302 of the holding device 120. In particular, the two holding elements 300, 302 and the light guide 104 are realized, for example, in one piece by way of appropriate processing of a glass plate, for instance a quartz plate.

The two holding elements 300, 302, in turn, rest on the base element 130 that is manufactured here as one piece, for instance out of silicon. The base element 130 has a recess 304, with the light guide 104 being held centrally over the recess 304 by the two holding elements 300, 302 such that said light guide has contact with the fluid that is as extensive as possible on all four sides.

According to an exemplary embodiment, the ends of the two holding elements 300, 302 that contact the light guide 104 are each realized with a cross section that tapers in the direction of the light guide 104 so as to minimize a contact face between the holding elements 300, 302 and the light guide 104.

By way of example, the straight light guide 104 is cut from a quartz plate and anchored to a silicon wafer as a base element 130 by way of two carriers in the form of the holding elements 300, 302.

The free-standing light guide 104 only consists of core material and it is suspended, for example, on four carriers by way of the two U-shaped holding elements 300, 302. By way of example, the holding elements 300, 302 are anchored on a silicon substrate as a base element 130 by way of wafer bonding, wherein a region of the base element 130 lying opposite the light guide 104 is exposed, for example by etching the recess 304.

The free-standing, light-guiding system in the form of the light guide 104 is surrounded by, for instance, air or any other suitable gas or else a liquid medium. Here, optical components such as splitters, couplers or mode mixers may be integrated directly into the light-guiding system.

Figure 5:
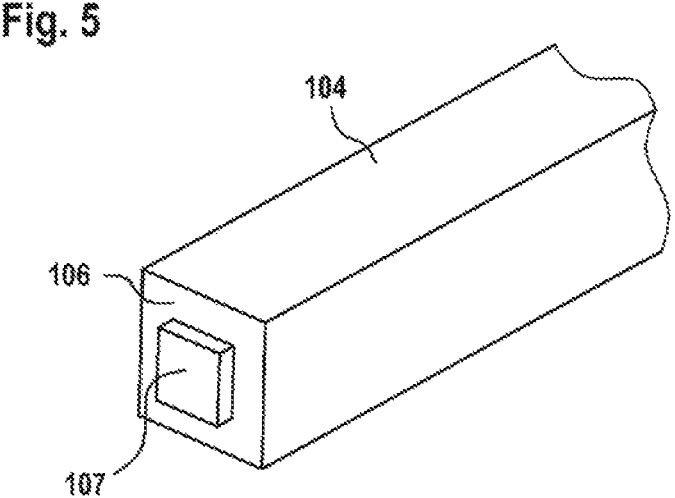
FIG. 5 shows a schematic illustration of a portion of a light guide according to an exemplary embodiment.

In contrast to conventional MEMS technologies, which are typically used for producing planar light guides, for example by means of thin layer deposition (plasma-enhanced chemical vapor deposition, abbreviated PECVD), the entire substrate thickness, for example of a glass wafer, is used for light guidance in this case. As a result of the high cross-sectional area obtained thereby, more light can be coupled from the light source 107 into the light guide 104 during input coupling, for instance by way of butt coupling, as shown in FIG. 5.

Structures such as curves, branchings and Y-couplers are cut by etching processes or laser ablation, for example, with the cut being carried out through the entire substrate thickness.

By way of example, air with a refractive index of virtually 1 is used as surrounding medium. As a result, it is possible to obtain a large refractive index difference of approximately 0.5 when the light guide 104 is manufactured from glass. Using this, a high acceptance angle and a high light input coupling efficiency are obtained.

A further advantage of the large refractive index difference between core and air cladding consists of being able to realize tighter radii of curvature of approximately 1 mm, for example, in the case of quartz with a square cross-section of 300×300 m², wherein the radius of curvature may become smaller with increasing difference in refractive index. It is possible to save space on the wafer by way of tighter radii of curvature and consequently the system can be miniaturized further. A significant reduction in the minimum radius of curvature can be obtained, particularly in comparison with optical fibers which have a minimum bending radius that typically corresponds to 300 times to 600 times the cladding radius, i.e. a bending radius of at least 3 cm in the case of a cladding radius of more than 100 µm, for example.

Consequently, by using a fitting medium such as air, vacuum or oil as a cladding, it is possible to dispense with a second material in wavelength ranges of less than 250 nm, for example, in which only a few highly transmissive materials are known or in which materials with different refractive indices can only be connected with difficulties from a technological point of view. Here, the light guide 104 can be realized with a thickness of more than 100 µm.

It is possible to attach further optical elements such as, for instance, laser diodes, LEDs, photodiodes or optical fibers to the interfaces of the measurement system.

The light guide 104 should be held in the air with minimal contact. To this end, it is possible to use carriers as holding elements 300, 302, or else bumps, i.e. metal spheres, in particular made out of a reflective material, that are placed below the light guide 104. The cross-sectional area of the holding elements 300, 302 scales with the light losses induced by the holding elements 300, 302 and it should therefore be minimized. By way of example, for the purposes of minimizing a contact area, the light guide 104 can be mounted between two substrates which are coated by pyramid-like structures, for example, and therefore only have contact with the light guide 104 at the tips. Alternatively, the light guide 104 is clamped directly and without further carrier elements between the light source 107 and the target, for instance a detector or a measurement cell. In branched systems, it is also conceivable for the light guide branches to act simultaneously as light-guiding and mechanical carrier structures by virtue of the light guide branches being anchored at their ends to sources, detectors and similar elements, as can be seen in, for instance, FIG. 1.

Figure 4:
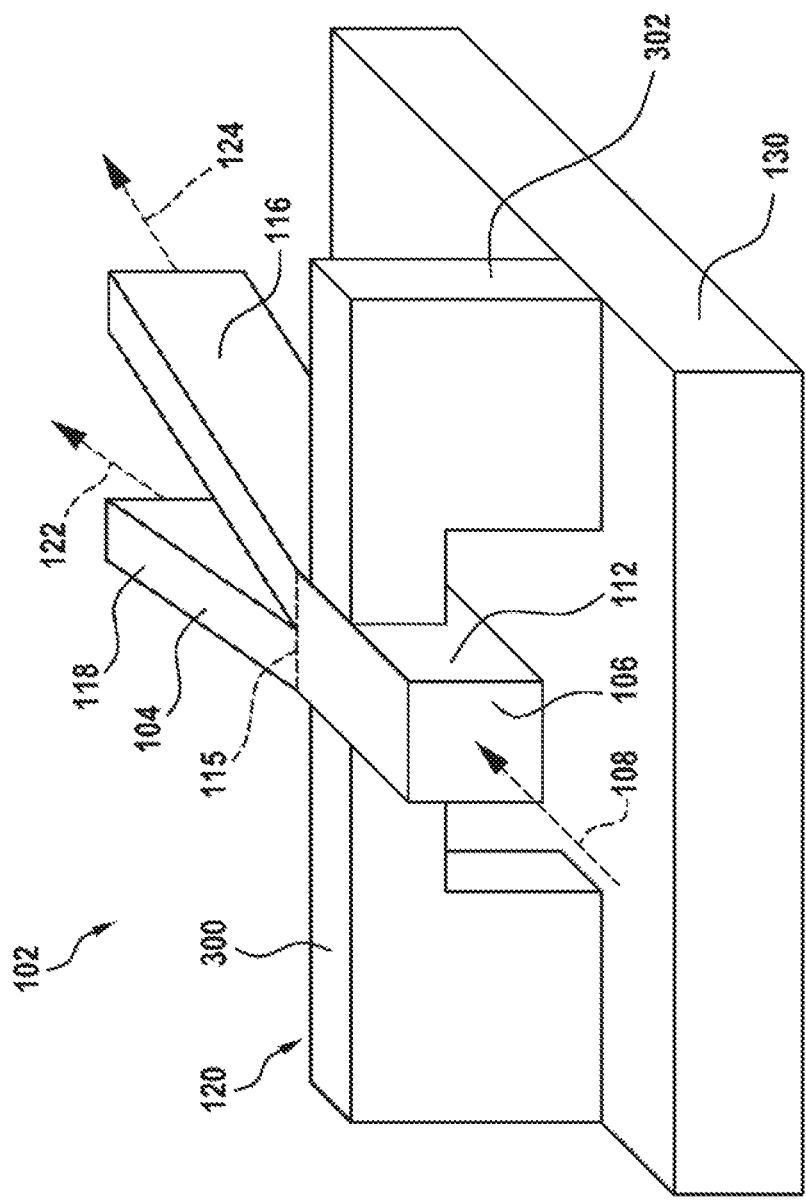
FIG. 4 shows a schematic illustration of a light guide apparatus according to an exemplary embodiment.

The structure of the light guide 104 and of further elements such as, for instance, curves or a Y-coupler, as shown in FIG. 4, is manufactured e.g. by cutting out a corresponding form from a planar substrate such as a wafer or a plate. Here, the holding elements 300, 302 can be structured in the same manufacturing step as the light guide 104. The number and form of the holding elements 300, 302 is based on the size or weight of the light guide 104 and on the respective field of application. In FIG. 3, the holding elements 300, 302 are attached to the light guide 104 at right angles in an exemplary manner. Light losses can be minimized by selecting a suitable angle between the holding elements 300, 302 and the light guide 104.

Figure 6:
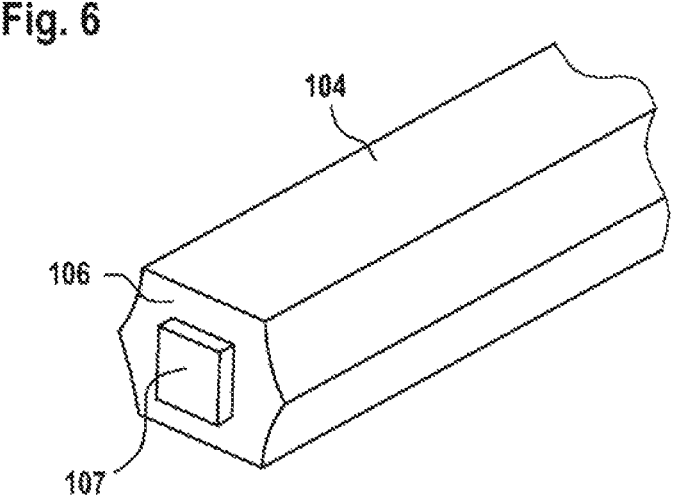
FIG. 6 shows a schematic illustration of a portion of a light guide according to an exemplary embodiment.

By way of example, very pure fused silica is suitable as a light-guiding material for the purposes of guiding UV light. By way of example, it can be structured by dry etching processes or laser ablation. In comparison with dry etching processes, wet etching with hydrofluoric acid (HF) represents a fast and cost-effective alternative. By etching the free-standing light guide 104 from both sides, it is possible to produce the light guide 104 with a hexagonal cross-section, as shown in FIG. 6. Alternatively, the light guide 104 may also be structured by mold casting or compression molding. A further structuring option consists of combining laser irradiation for material modification purposes in desired regions with a subsequent etching process, in which the regions modified by the laser irradiation have a higher etching rate and therefore are able to be etched selectively in relation to the non-irradiated regions (example: selective laser etching). By way of this technology, it is also possible to produce round and further arbitrary light guide cross sections.

Polymers that are transparent in a desired wavelength range, for instance special silicones in the deep UV range, can also be structured using the aforementioned methods. By way of example, such materials are processed, to this end, in typical processes of polymer treatment such as e.g. injection molding or extrusion.

Depending on the embodiment, the light guide 104 may also be structured with the aid of machining operations such as (micro-)milling or turning from an initial material, for example.

As an alternative to planar substrates as an initial material, use can also be made of wavy or other three-dimensionally formed substrates to be cut out so as to realize not only planar but also three-dimensional light guides. The production of a 3-D light guide formed as desired by casting the initial material into an appropriate mold is also conceivable. The normally complicated process step of molding a homogeneous cladding layer around a core, for instance by doping or depositing layers, can be dispensed with by the use of a fluid around the light guide.

In order to avoid changes in the refractive index of the air sheath as a result of changes in air pressure, humidity temperature and hence in order to avoid changes in the coupled-in and transmitted amount of light, or else in order to avoid the deposition of dust or condensate, the light guide 104 and the medium surrounding the latter may be arranged in a corresponding fluid-tight housing.

As shown in FIG. 2, the measurement system according to an exemplary embodiment is realized with a mode mixer for homogenizing the spatial beam distribution and with various splitters. As a result, the measurement system is suitable, in particular, for the application as a light-guiding system for the (exhaust) gas sensor system in (UV) absorption spectroscopy. Accordingly, the light is initially homogenized or mixed, and subsequently split, with some of the light being guided onto the reference detector. The other part is guided into a measurement cell, in which the gas-concentration-dependent absorption takes place. The light emanating from the measurement cell is now guided, in turn, to a measurement detector. Optionally, the light-guiding system is connected to the measurement cell by way of intermediate connections made of optical fibers. As a result, it is possible to bridge relatively long light paths and as a result it is possible to decouple heat-sensitive components such as light sources and detectors, for example, from high-temperature regions such as, for example, the exhaust branch. By way of example, to this end, the light source 107 emits UV light with a wavelength of 227 nm, with one part being guided to the reference detector and the other part being coupled into an optical fiber and guided to the measurement cell in the exhaust branch.

Light-emitting diodes, in particular, are suitable as light sources for use in compact and cost-critical products. If use is made of light-emitting diodes, the light proportion coupled into the light guide 104 may be restricted on account of the broad spatial emission characteristic. For instance, the so-called butt coupling is suitable as an input coupling method. Here, an end facet of the light guide 104 is placed directly on a planar side of the LED chip, with the light losses being reduced as the guide cross-sectional area increases in comparison with the LED area.

In contrast to conventional planar light guides with typical layer thicknesses of a few micrometers and typical dimensions of LED chips in the region of several hundred micrometers, the use of a light guide apparatus according to one of the exemplary embodiments described here makes it possible to dispense with additional focusing elements such as lens systems or development-intensive and cost-intensive input coupling techniques such as the input coupling by way of diffraction gratings. In contrast to optical fibers with layer thicknesses of 50 to 500 micrometers, for example, in the core and bending radii of the order of centimeters, the light guide 104 is significantly more manageable with a relatively large acceptance angle. Moreover, the light guide 104 can be produced with less outlay.

FIG. 4 shows a schematic illustration of a light guide apparatus 102 according to an exemplary embodiment. In contrast to FIG. 3, the holding apparatus 120 according to FIG. 4 is realized with two L-shaped holding elements 300, 302, with respectively a first end of the two holding elements having contact with the base element 130 that is realized here as a simple plate and respectively a second end of the two holding elements having contact with the light guide 104. Like in FIG. 3, the light guide branch 104 is also held in a free-standing manner over the base element 130 by the two holding elements 300, 302 in FIG. 4.

In contrast to the light guide described on the basis of FIGS. 1 to 3, the main branch 112 of the light guide 104 shown in FIG. 4 splits in a Y-shaped manner into the two light guide branches 116, 118 at the branching point 115, with the free ends of the two light guide branches 116, 118 each pointing in a direction facing away from the input coupling portion 106. At the branching point 115, the light beam 108 is split into the first partial beam 122 and the second partial beam 124 in such a way that the first partial beam 122 is guided through the second light guide branch 118 and the second partial beam 124 is guided through the first light guide branch 116.

It is clear from FIG. 4 that the light guide 104 is held over the base element 130 at the main branch 112 by way of the two holding elements 300, 302.

FIG. 5 shows a portion of a light guide 104 according to an exemplary embodiment, for instance of a light guide as described above on the basis of FIGS. 1 to 4. It is possible to see the input coupling portion 106 with the light source 107 in the form of a light-emitting diode anchored thereon, with the light source 104 being embodied significantly smaller than the input coupling portion 106.

In the butt coupling between the light source 107 and the light guide 104 shown in FIG. 5, the light source 107 has an emission area of 200×200 $\mu m^2$, for example, and the light guide 104 has a thickness of 350 µm, for example.

FIG. 6 shows a portion of a light guide 104 according to an exemplary embodiment. In contrast to FIG. 5, the light guide 104 according to FIG. 6 is realized with an approximately hexagonal cross section.

FIG. 6 shows, in an exemplary manner, an isotropic etching profile of an HF-etched quartz light guide 104, with the light guide 104 being etched on both sides from above and below and consequently having a hexagonal-like cross section.

Figure 7:
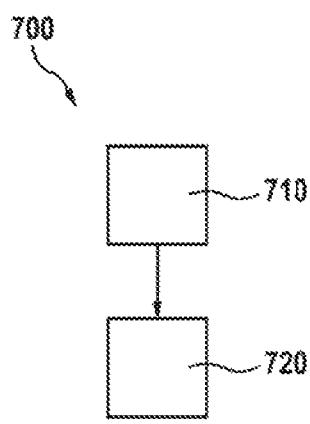
FIG. 7 shows a flowchart of a method for producing a light guide apparatus according to an exemplary embodiment.

FIG. 7 shows a flowchart of a method 700 for producing a light guide apparatus according to an exemplary embodiment. By way of example, the method 700 can be carried out to produce a light guide apparatus described on the basis of FIGS. 1 to 6. To this end, the light guide is formed in a step 710 by processing a substrate, provided in a provision step preceding step 710, made of a light-guiding, in particular transparent material, for instance a glass or polymer plate. By way of example, this is effectuated in a corresponding cutting or etching method. In a further step 720, the light guide is placed in the holding device, which is e.g. likewise provided in the provision step, and connected to the latter with a force fit, in an interlocking manner or in an integrally bonded manner, depending on the embodiment.

Alternatively, both the light guide and the holding device are formed in step 710 by processing the substrate. In particular, the light guide and the holding device are formed as a single part from the substrate in the same manufacturing step. Depending on the embodiment, the light guide is shaped on the holding device or the holding device is shaped on the light guide in the process, with it being possible for the light guide and the holding device to be shaped either simultaneously or in succession. Accordingly, step 720 may be dispensed with here.

If an exemplary embodiment comprises an "and/or" link between a first feature and a second feature, this should be read such that the exemplary embodiment has both the first feature and the second feature according to one embodiment and has either only the first feature or only the second feature according to a further embodiment.

The invention claimed is:

1. A light guide apparatus for guiding a first light beam between a light source and a measuring unit, which contains a gas or substance and is configured for measuring a gas concentration of the gas or substance concentration of the substance, the light guide apparatus comprising:
   a light guide including:
      at least one input coupling portion configured to couple-in the first light beam and to face the light source; and
      an output coupling portion configured to decouple the first light beam and to face the measuring unit,
      wherein the light guide is configured to guide the first light beam between the at least one input coupling portion and the output coupling portion via total-internal reflection at an interface to a fluid or material surrounding the light guide and having a first refractive index that is lower than a second refractive index of the light guide; and
   a holding device that holds the light guide in the fluid such that at least a main proportion of a surface of the light guide contacts the fluid, the holding device includes at least one first holding element and one second holding element, and the light guide is clamped between the at least one first holding element and the one second holding element.

2. The light guide apparatus as claimed in claim 1, further comprising:
   a base element on which the holding device is arranged, wherein the base element is manufactured from silicon or a silicon-containing material.

3. The light guide apparatus as claimed in claim 1, wherein the light guide and the holding device have an integral embodiment and/or are embodied from the same material.

4. The light guide apparatus as claimed in claim 1, wherein:
   the at least one input coupling portion is defined by a cross-sectional area of a first end of the light guide; and
   the output coupling portion is defined by a cross-sectional area of a second end of the light guide.

5. The light guide apparatus as claimed in claim 1, wherein the light guide and/or the holding device is formed from glass and/or a polymer.

6. The light guide apparatus as claimed in claim 1, further comprising:
a temperature regulating unit configured to actively cool, passively cool, actively heat, and/or passively heat the light source, the light guide, and/or the measuring unit.

7. The light guide apparatus as claimed in claim 1, wherein the at least one first holding element and/or the one second holding element has a U-shaped or L-shaped configuration.

8. The light guide apparatus as claimed in claim 1, wherein the at least one first holding element and/or the one second holding element has a cross section that tapers in a direction of the light guide at least one contact point at which the at least one first holding element and/or the one second holding element contacts the light guide.

9. The light guide apparatus as claimed in claim 1, wherein:
the first light beam is coupled-in via the at least one input coupling portion or the output coupling portion; and
the light guide further includes at least one branching point, at which at least one light guide branch branches off from the light guide, the at least one light guide branch configured to at least one of deflect and split the first light beam into at least two partial beams.

10. The light guide apparatus as claimed in claim 1, wherein:
the light guide further includes at least one first light guide branch arranged at least one first branching point and at least one second light guide branch arranged at least one second branching point; and
the first branching point is configured to split the first light beam, coupled-in via the at least one input coupling portion, into a first partial beam and a second partial beam so as to steer the first partial beam to the output coupling portion and so as to steer the second partial beam into the first light guide branch, and
the second branching point is configured to steer a second light beam, which is reflected from the measuring unit and coupled-in via the output coupling portion, into the second light guide branch and/or split the second light beam into a third partial beam and a fourth partial beam so as to steer the third partial beam toward the at least one input coupling portion and so as to steer the fourth partial beam into the second light guide branch.

11. The light guide apparatus as claimed in claim 10, wherein the second branching point is configured to steer at least one of (i) the second light beam that is coupled-in via the output coupling portion and (ii) the fourth partial beam into a first direction that deviates from a second direction of at least one of the first light beam that is coupled-in via the at least one input coupling portion, the first partial beam, and the second partial beam.

12. The light guide apparatus as claimed in claim 1, wherein the light guide is configured to homogenize the first light beam.

13. A measurement system, comprising:
a light source from which a light beam emanates;
a light guide apparatus including:
a light guide having:
at least one input coupling portion arranged facing the light source and configured to couple-in the light beam; and
an output coupling portion configured to decouple the light beam,
wherein the light guide is configured to guide the light beam between the at least one input coupling portion and the output coupling portion via total-internal reflection at an interface to a fluid or a material surrounding the light guide and having a first refractive index that is lower than a second refractive index of the light guide; and
a holding device that holds the light guide in the fluid such that at least a main proportion of a surface of the light guide contacts the fluid, the holding device includes at least one first holding element and one second holding element, and the light guide is clamped between the at least one first holding element and the one second holding element; and
a measuring unit arranged facing the output coupling portion of the light guide, the measuring unit containing a gas or substance and is configured for measuring a gas concentration of the gas or a substance concentration of the substance.

14. A method for producing a light guide apparatus for guiding a light beam between a light source and a measuring unit, which contains a gas or substance and is configured for measuring a gas concentration of the gas or substance concentration of the substance, the method comprising:
forming a light guide having at least one input coupling portion and at least one output coupling portion by processing a substrate formed of a light-guiding material, the at least one input coupling portion configured to couple-in the light beam and to face the light source, and the at least one output coupling portion configured to decouple the light beam and to face the measuring unit; and
arranging the light guide in a holding device by clamping the light guide between at least one first holding element and at least one second holding element of the holding device; and
forming the light guide and the holding device by processing the substrate,
wherein the light guide is shaped on the holding device and/or the holding device is shaped on the light guide.

* * * * *